Figure 1:
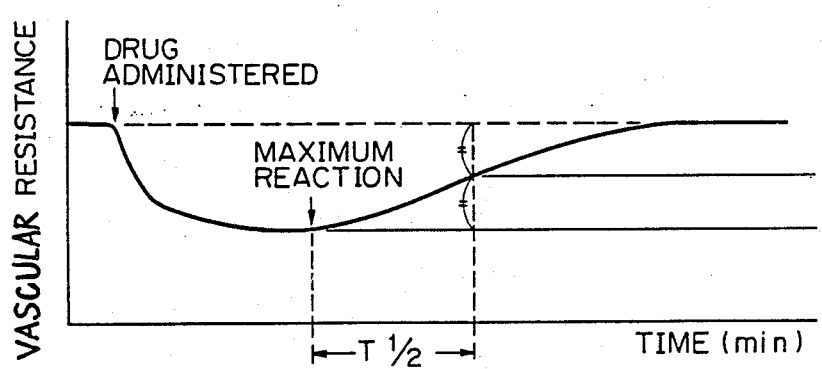

United States Patent [19]

Cho et al.

[11] Patent Number: 4,772,602

[45] Date of Patent: Sep. 20, 1988

[54] N-SUBSTITUTED 3,4-DIHYDROPYRIMIDINE DERIVATIVES AS AGENTS FOR TREATING DISORDERS OF CARDIOVASCULAR SYSTEM

[75] Inventors: Hidetsura Cho, Osaka; Akira Mizuno; Keiyu Shima, both of Kyoto, all of Japan

[73] Assignee: Suntory Limited, Osaka, Japan

[21] Appl. No.: 839,621

[22] Filed: Mar. 14, 1986

[30] Foreign Application Priority Data

Mar. 15, 1985 [JP] Japan .................. 60-51645

[51] Int. Cl.[4] ............... A61K 31/505; C07D 239/28; C07D 413/12
[52] U.S. Cl. ............... 514/235.8; 514/252; 514/256; 544/122; 544/333; 544/335
[58] Field of Search .............. 544/335, 122, 333; 514/269, 238, 252, 256

[56] References Cited

U.S. PATENT DOCUMENTS 4,532,248 7/1985 Franckowiak et al. ............ 514/302

OTHER PUBLICATIONS

*Medicinal Chemistry,* Burger, Edit., 2nd Ed., 1960, pp. 565-571, 579-581, 600 and 601.
Cho et al., J. Org. Chem., 50, pp. 4227-4230, 1985.
March, *Advanced Organic Chemistry,* Ed., 1977, pp. 361-362.

*Primary Examiner*—Mary C. Lee
*Assistant Examiner*—Kurt G. Briscoe
*Attorney, Agent, or Firm*—Cushman, Darby & Cushman

[57] ABSTRACT

A N-substituted 3,4-dihydropyrimidine derivative of the formula (1):

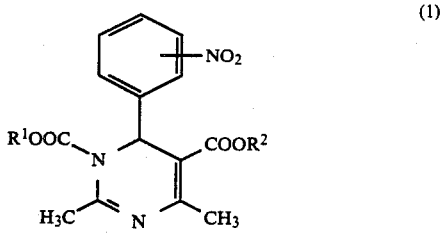

Wherein $R^1$ is —$(CH_2)_n$—X; X is substituted aminoethyl, substituted sulfideethyl, substituted or nonsubstituted heterocyclo-ethyl wherein the ethylene group is directly bonded to a hetero atom in the heterocyclic ring, or substituted or nonsubstituted heterocyclomethyl wherein the methylene group is directly bonded to a carbon atom in the heterocyclic ring; n is an integer from 0 to 8; $R^2$ is straight, branched cyclic or cyclostraight alkyl having from one to thirteen carbon atoms, or aralkyl having from seven to thirteen carbon atoms and pharmacologically acceptable acid additional salts thereof have substantially strong and long lasting effects. Therefore the compounds are useful as agents for treating disorders of the cardiovascular system, and are useful, for example, as antihypertensive agents, circulation improvers and antianginal agents.

A process for producing the above compounds economically and effectively is also disclosed.

2 Claims, 1 Drawing Sheet

N-SUBSTITUTED 3,4-DIHYDROPYRIMIDINE DERIVATIVES AS AGENTS FOR TREATING DISORDERS OF CARDIOVASCULAR SYSTEM

This invention relates to N-substituted 3,4-dihydropyrimidine derivatives of the formula (1):

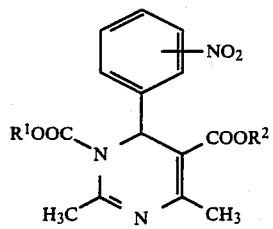
(1)

wherein $R^1$ is $-(CH_2)_n-X$; X is substituted aminoethyl, substituted sulfide-ethyl, substituted or non-substituted heterocyclo-ethyl wherein the ethylene group is directly bonded to a hetero atom in the heterocyclic ring, or substituted or non-substituted heterocyclomethyl wherein the methylene group is directly bonded to a carbon atom in the heterocyclic ring; n is an integer from 0 to 8; $R^2$ is straight, branched, cyclic or cyclo-straight alkyl having from one to thirteen carbon atoms, or aralkyl having from seven to thirteen carbon atoms and pharmacologically acceptable acid addition salts thereof, a process for production thereof, and an agent for treating disorders of the cardiovascular system.

Since the above dihydropyrimidine derivatives of the formula (1) have a strong and long lasting vasodilative effect, said compounds are useful as agents for treating disorders of the cardiovascular system, for example, as an anti-hypertensive agent, a cerebral circulation improver and an antianginal agent.

Currently it is being bound that calcium antagonists (Ca++ antagonists), which had been spotlighted as new agents for treating disorders of the cardiovascular system, have a variety of pharmacological effects and are active not only against hypertension, angina pectoris, cerebral circulation disorders and arrhythmia but also in preventing arteriosclerosis and potentiating the effects of carcinostatic agents. Thus therapeutic uses of Ca++ antagonists continue to increase.

Ca++ antagonists which have been known include Nifedipine, Nicardipine, Verapamil, Diltiazem and the like.

Up to this day, however, dihydropyrimidine derivatives have not often been investigated. Only a few references disclose said derivatives. [For example refer to Silversmith, E. F. J., Org. Chem., 27, 4090 (1962), Nasipuri, D. et al., Synthesis 1073 (1982), Kashima, C., Tetrahedron Letters 209 (1983) and Japanese Patent Public Disclosure No. 73572/59 (Bayer, A.G.)]

This can be considered to be due to the instability and tautomerism of the dihydropyrimidine derivatives. But there is room for improvement in the properties of the above-mentioned Ca++ antagonists such as duration of action, organ-selectivity, stability against light, heat etc. and with respect to side effects.

The inventors thoroughly investigated the Ca++ antagonists which are currently considered to be important. As a result we found that N-substituted 3,4-dihydropyrimidine derivatives have excellent vasodilative effects and high stability. (Refer to Japanese Patent Public Disclosure No. 214778/85, 246376/85, and 252471/85 and 43171/86.) However, the inventors more eagerly investigated the Ca++ antagonists which have the most excellent vaodilative effects and stability over a long term and reduced toxicity levels. As a result we have found that the N-substituted-3,4-dihydropyrimidine derivatives of the formula (1) not only have excellent stability and strong vasodilative effects but also long-term duration.

The present invention provides N-substituted 3,4-dihydropyrimidine derivatives of the formula (1) and pharmaceutically acceptable acid addition salts thereof.

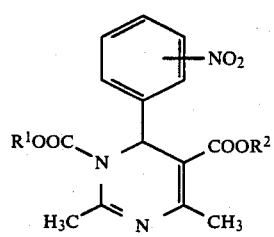
(1)

wherein $R^1$ and $R^2$ are as defined above.

Dihydropyrimidine derivatives of the formula:

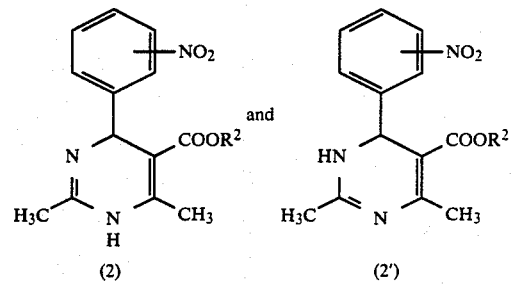

wherein $R^2$ is as defined above, and which are tautomeric isomers, have vasodilative effects too. But the compounds of the formula (1) were synthesized in order to obtain compounds having higher stability and pharmacological activity.

N-substituted 3,4-dihydropyrimidine derivatives of the formula (1) can be prepared in the following procedures:

(i) Tautomeric isomers of the formula (2) and (2'):

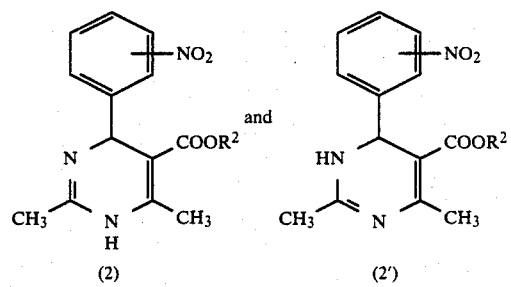

wherein $R^2$ is as defined above may be prepared by the following method:

A compound of the formuula $R^2OH$ wherein $R^2$ is as defined above is heated with one equivalent amount of diketene at 100° C.-200° C., preferably 120° C. for 30-60 minutes to give β-ketoester of the formula (3):

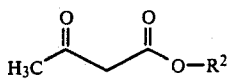

wherein $R^2$ is as defined above.

Alternatively, a compound of the formula (3) can be obtained by treating a compound of the formula $R^2OH$ in the presence of an equivalent amount of a base such as trialylamine at room temperature or treating said compound with said diketene at 0° C., or reacting said compound with diketene in the presence of sodium hydride or potassium hydride.

Benzaldehyde wherein the benzene ring is substituted with nitro group is added to the β-ketoester (3) and the mixture is subjected to dehydration-condensation to produce a benzylidene compound of the formula (4)

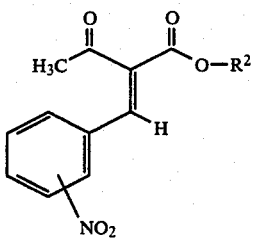

wherein $R^2$ is as defined above.

The benzylidene (4) is condensated with acetamidine or acetamidine hydrochloride to produce a tetrahydropyrimidine compound (5) of the formula:

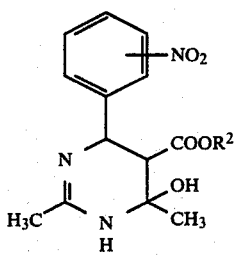

In order to obtain the compound (5), the above condensation above is carried out in the presence of a base. Preferable bases for use in this procedure include metal alkoxides and metal hydride and suitable solvents include alcohols, ethers and dimethylformamide.

The tetrahydropyrimidine (5) is heated in the presence of a catalyst such as p-toluenesulfonic acid, boron trifluoride or camphor-sulfonic acid, or heated with silicagel, alumina or molecular sieves to produce compounds represented by the formulae (2) and (2').

The thus obtained compounds may be purified by a conventional puurification method such as adsorption chromatography, ion-exchange chromatography, partition chromatography, distillation or recrystallization. Alternatively, the dihydropyrimidine derivatives of the formulae (2) and (2') may be crystallized as salts with an inorganic acid such as hydrochloric acid, sulfuric acid or phosphoric acid, or an organic acid such as oxalic acid, tartaric acid, succinic acid or maleic acid and may be purified by recrystallization.

(ii) Preparation of N-substituted 3,4-dihydropyrimidine derivatives:

The compound represented by the formulae (2) and (2') obtained in the above (i) is dissolved in an organic solvent such as hydrocarbon chlorides, aromatic hydrocarbons or ethers and the solution is added to a solution of phosgene or phosgene dimer in an organic solvent at a temperature not higher than 0° C., preferably $-10°\sim-35°$ C. in the presence of a base, for example, trialkylamine, preferably triethylamine, sodium hydride or potassium hydride. After the reaction is completed, a solution of a nitrogen-containing alcohol compound of the formula $R^1OH$ wherein $R^1$ is as defined above is further added to the reaction to afford the compound of the formula (1). The organic solvents used in this procedure include any solvents which do not affect the reaction, preferably ethers and hydrocarbon chlorides.

The substituent $R^2$ at the position 5 of the N-substituted 3,4-dihydropyrimidine derivatives (1) can be exemplified by straight, branched or cyclic alkyl having from one to thirteen carbon atoms or an aralkyl having from seven to thirteen carbon atoms such as benzyl, phenethyl, phenylpropyl, phenylbutyl, phenylpentyl or phenylhexyl.

The substituent $R^1$ of the ester residue at the position 3 of said derivative is represented by the formula $-(CH_2)_n-X$ wherein n is an integer from 0 to 8. When X is

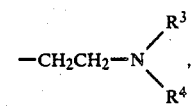

$R_3$ is exemplified by methyl, ethyl, propyl, isopropyl, butyl, sec-butyl, phenyl, naphthyl, benzyl, phenethyl, phenylpropyl, diphenylmethyl, naphthylmethyl, naphthylethyl, cinnamyl, cinnamylmethyl, pyridylmethyl or thienylmethyl and $R^4$ is exemplified by methyl, ethyl, propyl, isopropyl, butyl, sec-butyl, phenyl, naphthyl, benzyl, phenethyl, phenylpropyl, diphenylmethyl, naphthylmethyl, naphthylethyl, cinnamyl and cinnamylmethyl with the proviso that when one of $R^3$ and $R^4$ is alkyl, the other can also be aralkyl substituted with halogen, nitro or methoxy.

When X is heterocyclo-methyl or heterocyclo-ethyl, the heterocyclic ring is exemplified by pyrrolidinyl, piperidinyl, piperazinyl, morpholino, morpholinyl, thiomorpholinyl, thienyl, imidazolyl, pyridyl, pyrimidyl, quinolyl, isoquinolyl, tetrahydroisoquinolyl or indolyl and may be mono-substituted with alkyl, aryl, substituted aryl, aralkyl, substituted aralkyl or acyl. The phenyl ring of the above mono-substituent may be substituted with nitro, iodo, chloro, dichloro, bromo, dibromo, fluoro, methoxy, dimethoxy, trimethoxy, trifluoromethyl, cyano or thiomethyl. Among the above-mentioned substituted piperazinyl groups, piperazinyl substituted at position 4 such as 4-benzylpiperazinyl, 4-benzhydrylpiperazinyl, 4-methylpiperazinyl, 4-ethylpiperazinyl, 4-butylpiperazinyl, 4-acetylpiperazinyl, 4-propionylpiperazinyl, 4-benzoylpiperazinyl, 4-cinnamoylpiperazinyl or 4-phenylpiperazinyl is suitable.

After the above reaction the products of the formula (1) of this invention can be purified by using conventional methods such as adsorption column chromatography, ion-exchange chromatography or recrystallization. Alternatively, the products can be treated with an inorganic acid such as hydrochloric acid, sulfuric acid or phosphoric acid, or an organic acid such as oxalic acid, succinic acid or malic acid to convert them to salts thereof, and then can be purified by recrystallization, adsorption chromatography or ion-exchange chromatography.

The thus obtained compounds of the formula (1), when administered intra arterially (i.a.) or intravenously (i.v.) and orally (p.o.), indicated a strong coronery vasodilative effect in isolated guinea pig hearts (Langendorff's method) (i.a.), and showed strong cerebral vasodilative and hypotensive effects in anesthetized dogs (i.v.), and in conscious spontaneously hypertensive rats (p.o.). And all of these effects are superior to known drugs such as Nicardipine in terms of potency and duration. Thus, the compounds are considered to be useful as agents for treating angina pectoris (myocardial infarction), disturbance of cerebral circulation and hypertension.

The compounds (1) of this invention can be administered alone or in combination with excipients in a variety of dosage forms such as tablets, troches, pills, granules, powders, capsules, ampules, suppositories and the like. The excipients include, for example, starch, dextrin, sucrose, lactose, silicic acid, carboxymethylcellulose, cellulose, geratin, polyvinylpyrrolidone, glycerin, agar, calcium carbonate, sodium bicarbonate, paraffin, cetyl alcohol, stearic acid esters, kaolin, bentonite, talc, calcium stearate, magnecium stearate, polyethyleneglycol, water, ethanol, isopropylalcohol, propyleneglycol and the like.

For parenteral administration, the compounds of this invention are converted into water soluble salts thereof and the salts are dissolved in sterile distilled water or sterile physiological saline and are filled in ampules to be used for injection. If necessary, stabilizing agents and/or buffering agents can be included in the ampules.

For oral administration, the optimum dose range of the compound (1) of this invention is 5–500 mg per day.

Of course, this dose range can be suitably changed depending upon the characteristics of the subjects including age, response, body weight, severity of disease etc.

This invention can be illustrated by the following examples but it should be understood that it is not limited to them. The temperatures stated are in °C. unless otherwise specified.

EXAMPLE 1

3-{2-(N-benzyl-N-methylamino)ethoxycarbonyl}-5-cyclopropylmethoxycarbonyl-2,6-dimethyl-4-(2-nitrophenyl)-3,4-dihydropyrimidine (1)

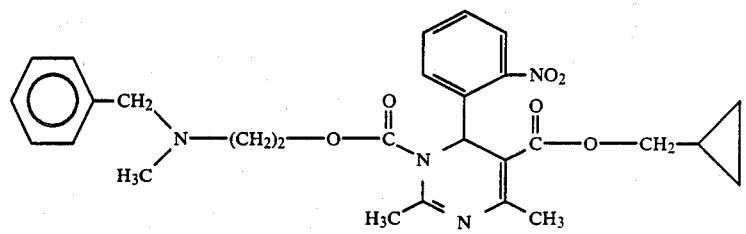

Trichloromethyl chloroformate (144 μl) was dissolved in 10 ml of tetrahydrofuran (THF). To the resulting solution, a mixture of 5-cyclo-propylmethoxycarbonyl-2,6-dimethyl-4-(2-nitrophenyl)-1,4-dihydropyrimidine (329 mg) and triethylamine (607 ml) in THF (20 ml) was added under stirring at −23° C., followed by stirring for an additional one hour. To the resulting mixture, 2-(N-benzyl-N-methylamino)ethan-1-ol (991 mg) in THF (10 ml) was added at 0° C., followed by stirring for one hour. The stirring was continued for one more hour at room temperature and, thereafter, the reaction mixture was diluted with a saturated aqueous solution of sodium chloride and subjected to extraction with chloroform. After drying the extract, the solvent was evaporated and the residue (1.32 g) was subjected to silica gel chromatography. By elution with 1% methanol-chloroform, the desired compound was obtained in an amount of 354 mg (yield: 68%). The physicochemical data of the compound are shown in Table 1.

The procedures of Example 1 were repeated in Examples 2–27 and the resulting compounds had the physicochemical data shown in Table 1.

TABLE 1

(1)

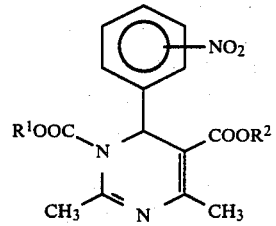

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | High resolution mass spectrum |
|---|---|---|---|---|---|---|
| 1 | (2-nitro group) R$^1$ = 2-(N—benzyl-N—methylamino)ethyl group R$^2$ = cyclopropylmethyl group | 68 | pale yellow oil | 1720 1700 | 0.10–0.25(2H,m), 0.35–0.55(2H,m), 1.00–1.15(1H,m), 2.21(3H,s), 2.33(3H,s), 2.48(3H,s), 2.63–2.83(2H,m), 3.53(2H,s), 3.82–3.96(2H,m), 4.15–4.30(1H,m), 4.38–4.50(1H,m), 6.91(1H,s), 7.18–7.80(9H,m) | For C$_{28}$H$_{32}$N$_4$O$_6$ cal'd: 520,5882 found: 520,5890 |
| 2 | (3-nitro group) | 32 | pale | 1720 | 0.10–0.35(2H,m), 0.40–0.65(2H,m), | For C$_{28}$H$_{32}$N$_4$O$_6$ |

TABLE 1-continued

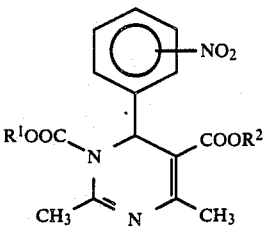
(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | High resolution mass spectrum |
|---|---|---|---|---|---|---|
| | R$^1$ = 2-(N—benzyl-N—methylamino)ethyl group<br>R$^2$ = cyclopropylmethyl group | | yellow oil | 1705 | 0.95–1.25(1H,m), 2.27(3H,s), 2.40(3H,s), 2.48(3H,s), 2.60–2.90(2H,m), 3.55(2H,s), 3.85–4.10(2H,m), 4.20–4.55(2H,m), 6.31(1H,s), 7.15–7.40(5H,m), 7.45(1H,t,J=8Hz), 7.65(1H,d,J=8Hz), 8.05–8.25(2H,m) | cal'd: 520,5882<br>found: 520,5878 |
| 3 | (2-nitro group)<br>R$^1$ = 2-(N—benzyl-N—methylamino)ethyl group<br>R$^2$ = ethyl group | 78 | pale yellow oil | 1735<br>1710 | 1.19(3H,t,J=7Hz), 2.21(3H,s), 2.27(3H,s), 2.32(3H,s), 2.60–2.82(2H,m), 3.56(2H,s), 4.05–4.50(4H,m), 6.88(1H,s), 7.20–7.80(9H,m) | For C$_{26}$H$_{30}$N$_4$O$_6$<br>cal'd: 494,5501<br>found: 494,5515 |
| 4 | (2-nitro group)<br>R$^1$ = 3-(dimethylamino)-propyl group<br>R$^2$ = ethyl group | 88 | pale yellow oil | 1720<br>1700 | 1.23(3H,t,J=7Hz), 1.80–1.95(2H,m), 2.21(6H,s), 2.33(2H,t,J=7Hz), 2.35(3H,s), 2.45(3H,s), 4.08–4.38(4H,m), 6.86(1H,s), 7.38–7.80(4H,m) | For C$_{21}$H$_{28}$N$_4$O$_6$<br>cal'd: 432,2009<br>found: 432,2037 |
| 5 | (2-nitro group)<br>R$^1$ = 2-{N—(4-methoxy-benzyl)-N—methyl-amino}ethyl group<br>R$^2$ = cyclopropylmethyl group | 81 | pale yellow oil | 1720<br>1695 | 0.10–0.25(2H,m), 0.35–0.55(2H,m), 1.00–1.15(1H,m), 2.19(3H,s), 2.33(3H,s), 2.48(3H,s), 2.65–2.80(2H,m), 3.46(2H,s), 3.77(3H,s), 3.85–3.95(2H,m), 4.15–4.50(2H,m), 6.92(1H,s), 6.75–7.80(8H,m) | For C$_{29}$H$_{34}$N$_4$O$_7$<br>cal'd: 550,6146<br>found: 550,6152 |
| 6 | (2-nitro group)<br>R$^1$ = 2-{N—(2-chloro-benzyl)-N—methyl-amino}ethyl group<br>R$^2$ = cyclopropylmethyl group | 23 | pale yellow oil | 1730<br>1700 | 0.10–0.20(2H,m), 0.35–0.50(2H,m), 1.00–1.15(1H,m), 2.27(3H,s), 2.32(3H,s), 2.47(3H,d,J=1Hz), 2.70–2.90(2H,m), 3.67(3H,s), 3.80–3.95(2H,m), 4.15–4.50(2H,m), 6.89(1H,s), 7.10–7.80(8H,m) | For C$_{28}$H$_{31}$ClN$_4$O$_6$<br>cal'd: 555,0333<br>found: 555,0356 |
| 7 | (2-nitro group)<br>R$^1$ = 2-{N—methyl-N—(4-nitrobenzyl)amino}-ethyl group<br>R$^2$ = cyclopropylmethyl group | 18 | pale yellow oil | 1730<br>1700 | 0.10–0.25(2H,m), 0.35–0.55(2H,m), 1.00–1.20(1H,m), 2.24(3H,s), 2.34(3H,s), 2.48(3H,s), 2.70–2.90(2H,m), 3.65(2H,s), 3.91(2H,d,J=7Hz), 4.15–4.25(1H,m), 4.40–4.55(1H,m), 6.90(1H,s), 7.40–8.20(8H,m) | For C$_{28}$H$_{31}$N$_5$O$_8$<br>cal'd: 565,5858<br>found: 565,5861 |
| 8 | (2-nitro group)<br>R$^1$ = 2-(N—diphenyl-methyl-N—methyl-amino)ethyl group<br>R$^2$ = cyclopropylmethyl group | 77 | pale yellow oil | 1725<br>1700 | 0.05–0.25(2H,m), 0.30–0.55(2H,m), 0.95–1.20(1H,m), 2.20(3H,s), 2.33(3H,s), 2.48(3H,s), 2.55–2.85(2H,m), 3.80–4.00(2H,m), 4.18–4.30(1H,m), 4.30–4.45(1H,m), 4.47(1H,s), 6.91(1H,s), 7.10–7.60 (13H,m), 7.78(1H,brd,J=2Hz) | For C$_{34}$H$_{36}$N$_4$O$_6$<br>cal'd: 596,6867<br>found: 596,6846 |
| 9 | (2-nitro group)<br>R$^1$ = 5-(N—methyl-N—benzylamino)pentyl group<br>R$^2$ = cyclopropylmethyl group | 80 | pale yellow oil | 1725<br>1700 | 0.10–0.25(2H,m), 0.40–0.55(2H,m), 1.00–1.20(1H,m), 1.30–1.85(6H,m), 2.17(3H,s), 2.35(3H,s), 2.36(2H,t,J=7Hz), 2.46(3H,s), 3.46(2H,s), 3.80–4.30(4H,m), 6.90(1H,s), 7.20–7.80(9H,m) | For C$_{31}$H$_{38}$N$_4$O$_6$<br>cal'd: 562,6691<br>found: 562,6701 |
| 10 | (2-nitro group)<br>R$^1$ = 2-(N—benzyl-N—methylamino)ethyl group<br>R$^2$ = isopropyl group | 37 | pale yellow oil | 1725<br>1700 | 1.04(3H,d,J=6Hz), 1.24(3H,d,J=6Hz), 2.22(3H,s), 2.30(3H,s), 2.48(3H,s), 2.62–2.86(2H,m), 3.53(2H,s), 4.10–4.50(2H,m), 4.95–5.10(1H,m), 6.88(1H,s), 7.15–7.80(9H,m) | For C$_{27}$H$_{32}$N$_4$O$_6$<br>cal'd: 508,5771<br>found: 508,5767 |
| 11 | (2-nitro group)<br>R$^1$ = 2-(N—4-fluorobenzyl-N—methylamino)ethyl group<br>R$^2$ = cyclopropylmethyl group | 45 | pale yellow oil | 1720<br>1700 | 0.10–0.20(2H,m), 0.40–0.50(2H,m), 1.00–1.15(1H,m), 2.20(3H,s), 2.34(3H,s), 2.48(3H,s), 2.60–2.83(2H,m), 3.49(2H,s), 3.85–3.97(2H,m), 4.13–4.50(2H,m), 6.88(1H,s), 7.20–7.80(8H,m) | For C$_{28}$H$_{31}$FN$_4$O$_6$<br>cal'd: 538,5787<br>found: 538,5799 |
| 12 | (2-nitro group)<br>R$^1$ = 2-(N—benzyl-N—methylamino)ethyl group | 37 | pale yellow oil | 1720<br>1700 | 0.85(3H,t,J=7Hz), 1.05–1.35(10H,m), 1.50–1.65(2H,m), 2.21(3H,s), 2.31(3H,s), 2.48(3H,s), 2.60–2.85(2H,m), 3.53(2H,s), | For C$_{31}$H$_{40}$N$_4$O$_6$<br>cal'd: 564,6849<br>found: 564,6855 |

TABLE 1-continued

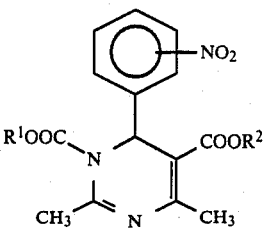

(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | High resolution mass spectrum |
|---|---|---|---|---|---|---|
| | $R^2$ = n-heptyl group | | | | 4.00–4.15(2H,m), 4.10–4.50(2H,m), 6.87(1H,s), 7.15–7.80(9H,m) | |
| 13 | (2-nitro group)<br>$R^1$ = 2-(N—benzyl-N—methylamino)ethyl group<br>$R^2$ = phenetyl group | 6 | pale yellow oil | 1730<br>1710 | 2.21(3H,s), 2.31(3H,s), 2.42(3H,s), 2.65–2.85(2H,m), 2.89(2H,t,J=7Hz), 3.53(2H,s), 4.18–4.50(4H,m), 6.86(1H,s), 7.00–7.80(14H,m) | For C$_{32}$H$_{34}$N$_4$O$_4$<br>cal'd: 538,6498<br>found: 538,6487 |
| 14 | (2-nitro group)<br>$R^1$ = 2-(N—benzyl-N—n-butylamino)ethyl group<br>$R^2$ = cyclopropylmethyl group | 54 | pale yellow oil | 1730<br>1710 | 0.12–0.18(2H,m), 0.40–0.47(2H,m), 0.84(3H,t,J=7Hz), 1.04–1.13(1H,m), 1.18–1.33(2H,m), 1.37–1.47(2H,m), 2.32(3H,s), 2.45(2H,t,J=7Hz), 2.47(3H,s), 2.77(2H,t,J=6Hz), 3.60(2H,s), 3.84–3.97(2H,m), 4.12–4.37(2H,m), 6.87(1H,s) 7.19–7.78(9H,m) | For C$_{31}$H$_{38}$N$_4$O$_6$<br>cal'd: 562,6691<br>found: 562,6687 |
| 15 | (2-nitro group)<br>$R^1$ = 2-(N—ethyl-anilino)ethyl group<br>$R^2$ = cyclopropylmethyl group | 66 | pale yellow oil | 1730<br>1705 | 0.14–0.23(2H,m), 0.42–0.50(2H,m), 1.06–1.17(1H,m), 1.15(3H,t,J=7Hz), 2.29(3H,s), 2.46(3H,s), 3.38(2H,q,J=7Hz), 3.51–3.72(2H,m), 3.86–3.99(2H,m), 4.22–4.43(2H,m), 6.61–6.72(3H,m), 6.83(1H,s), 7.12–7.79(6H,m) | For C$_{28}$H$_{32}$N$_4$O$_6$<br>cal'd: 520,2323<br>found: 520,2366 |
| 16 | (2-nitro group)<br>$R^1$ = 3-(N—benzyl-N—methylamino)propyl group<br>$R^2$ = cyclopropylmethyl group | 64 | pale yellow oil | 1730<br>1710 | 0.08–0.30(2H,m), 0.35–0.60(2H,m), 1.00–1.20(1H,m), 1.80–2.05(2H,m), 2.19(3H,s), 2.28(3H,s), 2.35–2.55(2H,m), 2.46(3H,s) 3.42(1H,d,J=13Hz),3.50(1H,d,J=13Hz),3.80–4.05(2H,m), 4.10–4.30(1H,m), 4.30–4.45(1H,m),6.86(1H,s),7.10–7.85(9H,m) | For C$_{29}$H$_{34}$N$_4$O$_6$<br>cal'd: 534,6152<br>found: 534,6173 |
| 17 | (2-nitro group)<br>$R^1$ = 2-{N—methyl-N—(2-phenylethyl)amino}-ethyl group<br>$R^2$ = cyclopropylmethyl group | 83 | pale yellow oil | 1725<br>1695 | 0.08–0.23(2H,m), 0.35–0.55(2H,m), 1.00–1.20(1H,m), 2.33(3H,s), 2.34(3H,s), 2.47(3H,s), 2.55–2.87(6H,m), 3.80–3.98(2H,m), 4.10–4.22(1H,m), 4.35–4.50(1H,m), 6.89(1H,s), 7.10–7.85(9H,m) | For C$_{29}$H$_{34}$N$_4$O$_6$<br>cal'd: 534,6152<br>found: 534,6150 |
| 18 | (2-nitro group)<br>$R^1$ = 2-{N-methyl-N—(3-phenylpropyl)amino}-ethyl group<br>$R^2$ = cyclopropylmethyl group | 77 | pale yellow oil | 1720<br>1695 | 0.08–0.25(2H,m), 0.36–0.55(2H,m), 1.00–1.18(1H,m), 1.65–1.83(2H,m), 2.24(3H,s), 2.35(3H,s), 2.35–2.45(2H,m), 2.43(3H,s), 2.51–2.63(2H,m), 2.63–2.79(2H,m),3.82–3.99(2H,m), 4.10–4.23(1H,m),4.34–4.48(1H,m), 6.89(1H,s), 7.10–7.82(9H,m) | For C$_{30}$H$_{36}$N$_4$O$_6$<br>cal'd: 548,6412<br>found: 548,6430 |
| 19 | (2-nitro group)<br>$R^1$ = (N—benzyl-2-pyrrolidinyl)methyl group<br>$R^2$ = cyclopropylmethyl group | 30 | pale yellow oil | 1730<br>1710 | As 2:1 mixture of isomers:<br>0.10–0.28(2H,m), 0.35–0.60(2H,m), 1.00–1.20(1H,m), 0.55–2.30(4H,m), 2.36, 2.43 & 2.46(total 6H, each s), 2.80–3.05(2H,m), 3.36(d, J=13Hz) & 3.45(d,J=13Hz) & 3.75–4.10(m) with total 5H, 4.10–4.30 & 4.30–4.45(total 2H, each m), 6.88 & 6.91(total 1H, each s), 7.15–7.85(9H,m) | For C$_{30}$H$_{34}$N$_4$O$_6$<br>cal'd: 546,6263<br>found: 546,6272 |
| 20 | (2-nitro group)<br>$R^1$ = 2-morpholinoethyl group<br>$R^2$ = cyclopropylmethyl group | 56 | pale yellow oil | 1730<br>1710 | 0.14–0.21(2H,m), 0.43–0.50(2H,m), 1.06–1.15(1H,m), 2.36(3H,s), 2.42–2.75(6H,m), 2.47(3H,s), 3.59–3.70(4H,m), 3.86–3.99(2H,m), 4.11–4.19(1H,m), 4.41–4.50(1H,m), 6.88(1H,s), 7.39–7.78(4H,m) | For C$_{24}$H$_{30}$N$_4$O$_7$<br>cal'd: 486,5272<br>found: 486,5281 |
| 21 | (2-nitro group)<br>$R^1$ = 2-(1,2,3,4-tetra-hydroisoquinolin-2-yl)ethyl group<br>$R^2$ = cyclopropylmethyl group | 71 | pale yellow oil | 1730<br>1700 | 0.10–0.25(2H,m), 0.40–0.55(2H,m), 1.00–1.15(1H,m), 2.33(3H,s), 2.42(3H,s), 2.73–2.95(6H,m), 3.67(2H,s), 3.85–3.98(2H,m), 4.22–4.60(2H,m), 6.89(1H,s), 6.95–7.80(8H,m) | For C$_{29}$H$_{32}$N$_4$O$_6$<br>cal'd: 532,5994<br>found: 532,5996 |
| 22 | (2-nitro group)<br>$R^1$ = 2-(4-ethyl-1- | 86 | pale yellow | 1720<br>1700 | 0.15–0.25(2H,m), 0.40–0.55(2H,m), 1.00–1.20(1H,m), 1.07(3H,t,J=7Hz), | For C$_{26}$H$_{35}$N$_5$O$_6$<br>cal'd: 513,5963 |

TABLE 1-continued (1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | High resolution mass spectrum |
|---|---|---|---|---|---|---|
|  | piperazinyl)ethyl group R$^2$ = cyclopropylmethyl group |  | oil |  | 2.36(3H,s), 2.47(3H,s), 2.30–2.80(12H,m), 3.85–4.00(2H,m), 4.10–4.52(2H,m), 6.88(1H,s), 7.40–7.80(4H,m) | found: 513,5976 |
| 23 | (2-nitro group) R$^1$ = 2-(4-benzhydryl-1-piperazinyl)ethyl group R$^2$ = cyclopropylmethyl group | 75 | pale yellow oil | 1718 1690 | 0.10–0.20(2H,m), 0.35–0.50(2H,m), 1.00–1.15(1H,m), 2.34(3H,s), 2.47(3H,s), 2.20–2.75(10H,m), 3.80–3.95(2H,m), 4.10–4.45(2H,m), 4.14(1H,s), 6.86(1H,s), 7.12–7.80(14H,m) | For C$_{37}$H$_{41}$N$_5$O$_6$ cal'd: 651,7664 found: 651,7684 |
| 24 | (2-nitro group) R$^1$ = 2-(4-benzyl-1-piperazinyl)ethyl group R$^2$ = cyclopropylmethyl group | 19 | pale yellow oil | 1725 1700 | 0.15–0.25(2H,m), 0.40–0.50(2H,m), 1.05–1.15(1H,m), 2.38(3H,s), 2.45(3H,s), 2.50–2.80(2H,m), 3.43(2H,s), 3.82–4.00(2H,m), 4.10–4.23(1H,m), 4.38–4.50(1H,m), 6.88(1H,s), 7.20–7.80(9H,m) | For C$_{31}$H$_{37}$N$_5$O$_6$ cal'd: 575,6678 found: 575,6687 |
| 25 | (2-nitro group) R$^1$ = 2-{4-(3,4,5-tri-methoxycinnamoyl)-1-piperazinyl}ethyl group R$^2$ = cyclopropylmethyl group | 54 | pale yellow oil | 1730 1700 | 0.15–0.25(2H,m), 0.40–0.55(2H,m), 1.05–1.20(1H,m), 2.37(3H,s), 2.46(3H,s), 2.46–2.82(6H,m), 3.55–3.80(4H,m), 3.88(3H,s), 3.90(6H,s), 4.15–4.22(1H,m), 4.43–4.55(1H,m), 6.74(2H,s), 6.74(1H,d,J=15Hz), 6.88(1H,s), 7.40–7.80(4H,m), 7.58(1H,d,J=15Hz) | For C$_{36}$H$_{43}$N$_5$O$_{10}$ cal'd: 705,7686 found: 705,7676 |
| 26 | (2-nitro group) R$^1$ = 2-{4-(3-trifluoro-methylphenyl)-1-piperazinyl}ethyl group R$^2$ = cyclopropylmethyl group | 81 | pale yellow oil | 1730 1700 | 0.10–0.25(2H,m), 0.40–0.55(2H,m), 1.00–1.20(1H,m), 2.36(3H,s), 2.45(3H,s), 2.55–2.85(6H,m), 3.05–3.30(4H,m), 3.85–4.00(2H,m), 4.10–4.25(1H,m), 4.50–4.60(1H,m), 6.89(1H,s), 7.00–7.80(8H,m) | For C$_{31}$H$_{34}$F$_3$N$_5$O$_6$ cal'd: 629,6394 found: 629,6371 |
| 27 | (2-nitro group) R$^1$ = 2-(2-pyridyl)ethyl group R$^2$ = isopropyl group | 64 | 97–98° C. (n-hexane/ether) | 1735 1705 | 1.05(3H,d,J=6Hz), 1.27(3H,d,J=7Hz), 2.18(3H,s), 2.44(3H,d,J=1Hz), 3.20(2H,t,J=7Hz), 4.45–4.75(2H,m), 5.02(1H,dq,J=7Hz), 6.82(1H,brs), 7.10–7.80(7H,m), 8.52(1H,d,J=2Hz) | For C$_{24}$H$_{26}$N$_4$O$_6$ cal'd: 466,4962 found: 466,4969 |

EXAMPLE 28

3-[2-{N-benzyl-N-(3-phenylpropyl)amino}ethoxycarbonyl]-5-cyclopropylmethoxycarbonyl-2,6-dimethyl-4-(2-nitrophenyl)-3,4-dihydropyrimidine (1)

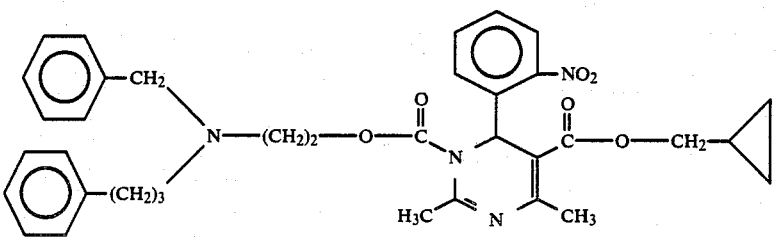

Method 1:

Trichloromethyl chloroformate (719 μl) was dissolved in 40 ml of tetrahydrofuran (THF). To the resulting solution, a mixture of 5-cyclopropylmethoxycarbonyl-2,6-dimethyl-4-(2-nitrophenyl)-1,4-dihydropyrimidine (1.65 g) and triethylamine (3.04 g) in THF (80 ml) was added under stirring at −23° C., followed by stirring for an additional one hour at −23° C. To the resulting mixture, 2-{N-benzyl-N-(3-phenylpropyl)amino}ethan-1-ol (6.73 g) in THF (40 ml) was added at 0° C., followed by stirring for 2 hour at room temperature. The reaction mixture was diluted with a saturated aqueous solution of sodium chloride and subjected to extraction with chloroform. After drying the extract, the solvent was evaporaed and the residue (ca. 12 g) was subjected to silica gel chromatography. By elution with a 1:1 mixture of ethyl acetate and n-hexane, the end compound was obtained in an amount of 2.14 g (yield: 69%).

Method 2:

Trichloromethyl chloroformate (300 μl) was dissolved in 30 ml of tetrahydrofuran (THF). To the resulting solution, a mixture of 5-cyclopropylmethoxycarbonyl-2,6-dimethyl-4-(2-nitrophenyl)-1,4-dihydropyrimidine (1.65 g) and triethylamine (3.04 g) in THF (70 ml) was added under stirring at −23° C., followed by stirring for an additional one hour at −23° C. To the resulting mixture, 2-{N-benzyl-N-(3-phenylpropyl)amino}ethan-1-ol (1.35 g) in THF (50 ml) was added at 0° C., followed by stirring for 2 hours at room temperature. The reaction mixture was diluted with a saturated aqueous solution of sodium chloride and subjected to extraction with chloroform. After drying the extract, the solvent was evaporated and the residue (ca. 4.6 g) was subjected to silica gel chromatography. By elution with a 1:2 mixture of ethyl acetate and n-hexane, the end compound was obtained in an amount of 1.51 g (yield: 48%).

The physical data of the end compound are shown in Table 2.

The procedures of method 1 and 2 were repeated in Examples 29–74. The data of the compounds prepared in Examples 29–74 are also listed in Table 2.

TABLE 2

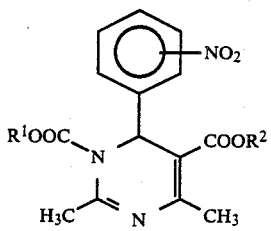

(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | Elemental analysis |
|---|---|---|---|---|---|---|
| 28 | (2-nitro group) R$^1$ = 2-{N—benzyl-N (3-phenylpropyl)- amino}ethyl group R$^2$ = cyclopropylmethyl group | 69 | pale yellow oil | 1720 1695 | 0.06–0.23(2H,m), 0.32–0.51(2H,m), 0.98–1.17(1H,m) 1.68–1.88(2H,m), 2.30(3H,s), 2.45(3H,s), 2.45–2.65 (4H,m), 2.78(2H,t,J=7Hz), 3.61 (2H,s), 3.81–3.97(2H,m), 4.11–4.24 (1H,m), 4.26–4.40(1H,m), 6.87(1H,s), 7.06–7.83(14H,m) | For C$_{36}$H$_{40}$N$_4$O$_6$ cal'd: C 69.21 H 6.45 N 8.97 found: C 69.25 H 6.55 N 8.81 |
| 29 | (2-nitro group) R$^1$ = 2-{N—benzyl-N— (3-phenyl-2-(E)— propenyl)amino}- ethyl group R$^2$ = cyclopropylmethyl group | 75 | pale yellow oil | 1725 1700 | 0.06–0.24(2H,m), 0.32–0.52(2H,m), 0.97–1.18(1H,m), 2.30(3H,s), 2.47(3H,s), 2.85(2H,t,J=6Hz), 3.29(2H,d,J=9Hz), 3.67(2H,s), 3.85–4.00(2H,m), 4.13–4.29(1H,m), 4.32–4.48(1H,m), 6.24(1H,dt,J=16Hz, 6Hz), 6.50(1H,d,J=16Hz), 6.89(1H,s), 7.14–7.80(14H,m) | |
| 30 | (2-nitro group) R$^1$ = 2-{N—methyl-N— (2-naphthylmethyl)- amino}ethyl group R$^2$ = cyclopropylmethyl group | 82 | pale yellow oil | 1700 | 0.05–0.23(2H,m), 0.30–0.52(2H,m), 0.95–1.18(1H,m), 2.25(3H,s), 2.33 (3H,s), 2.47 (3H,s), 2.66–2.92(2H,m), 3.69(2H,s), 3.80–4.00(2H,m), 4.18–4.38(1H,m), 4.40–4.55(1H,m), 6.92(1H,s), 7.32–7.92(11H,m) | |
| 31 | (2-nitro group) R$^1$ = 2-{N—methyl-N— (3-phenyl-2-(E)— propenyl)amino}- ethyl group R$^2$ = cyclopropylmethyl group | 88 | pale yellow oil | 1695 | 0.07–0.27(2H,m), 0.34–0.53(2H,m), 1.00–1.20(1H,m), 2.29(3H,s), 2.35 (3H,s), 2.46(3H,s), 2.63–2.88(2H,m), 3.20(2H,d,J=7Hz), 3.80–4.00(2H,m), 4.12–4.30(1H,m), 4.36–4.50(1H,m), 6.17(1H,dt,J=16Hz,7Hz), 6.49(1H,d, J=16Hz), 6.90(1H,s), 7.16–7.83(9H,m) | |
| 32 | (2-nitro group) R$^1$ = 2-{N—(3-phenyl- 2-(E)—propenyl-N— (2-thienylmethyl)- amino}ethyl group R$^2$ = cyclopropylmethyl group | 62 | pale yellow oil | 1730 1700 | 0.06–0.22(2H,m), 0.32–0.52(2H,m), 0.98–1.18(1H,m), 2.34(3H,s), 2.47(3H,s), 2.78–3.00(2H,m), 3.33(2H,d,J=7Hz), 3.80–4.00(2H,m), 3.89(2H,s), 4.13–4.28(1H,m), 4.35–4.50(1H,m), 6.22(1H,dt,J=16Hz, 7Hz), 6.54(1H,d,J=16Hz), 6.82–6.99 (2H,m), 6.92(1H,s), 7.15–7.82(10H,m) | |
| 33 | (2-nitro group) R$^1$ = 2-{N,N—bis(3- phenyl-2-(E)— propenylamino}ethyl group R$^2$ = cyclopropylmethyl group | 89 | pale yellow oil | 1720 1695 | 0.05–0.25(2H,m), 0.35–0.50(2H,m), 0.98–1.17(1H,m), 2.34(3H,s), 2.44(3H,s), 2.89(2H,t,J=6Hz), 3.42(4H,d,J=7Hz), 3.80–3.98(2H,m), 4.15–4.29(1H,m), 4.35–4.48(1H,m), 6.22(2H,dt,J=16Hz,7Hz), 6.52(2H,d, J=16Hz), 6.90(1H,s), 7.16–7.81(14H,m) | |
| 34 | (2-nitro group) | 50 | pale yellow | 1725 | 0.06–0.25(2H,m), 0.34–0.55(2H,m), | |

TABLE 2-continued

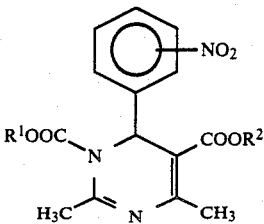

(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | Elemental analysis |
|---|---|---|---|---|---|---|
| | R$^1$ = 2-(N—benzyl-N—diphenylmethyl-amino)ethyl group<br>R$^2$ = cyclopropylmethyl group | | oil | 1700 | 1.00–1.18(1H,m), 2.24(3H,s), 2.47 (3H,s), 2.80–2.95(2H,m), 3.64(1H,d, J=14Hz), 3.72(1H,d,J=14Hz), 3.84–3.98(2H,m), 4.18(2H,t,J=7Hz), 4.93(1H,s), 6.81(1H,s), 7.20–7.80(19H,m) | |
| 35 | (2-nitro group)<br>R$^1$ = 2-{N—methyl-N—(2-pyridylmethyl)-amino}ethyl group<br>R$^2$ = cyclopropylmethyl group | 13 | pale yellow oil | 1735 1710 | 0.11–0.20(2H,m), 0.37–0.49(2H,m), 1.01–1.13(1H,m), 2.30(3H,s), 2.34 (3H,s), 2.48(3H,s), 2.73–2.91(2H,m), 3.72(2H,s), 3.83–3.96(2H,m), 4.17–4.25(1H,m), 4.42–4.51(1H,m), 6.90(1H,s), 7.11–8.54(8H,m) | |
| 36 | (3-nitro group)<br>R$^1$ = 2-{N—benzyl-N—(3-phenylpropyl)-amino}ethyl group<br>R$^2$ = cyclopropylmethyl group | 65 | pale yellow oil | 1725 | 0.12–0.25(2H,m), 0.42–0.55(2H,m), 1.06(1H,m), 1.70–1.86(2H,m), 2.36 (3H,s), 2.45(3H,s), 2.49–2.62(4H,m), 2.80(2H,t,J=6Hz), 3.62(2H,s), 3.85–4.01(2H,m), 4.30(2H,t,J=6Hz), 6.28(1H,s), 7.09–8.14(14H,m) | |
| 37 | (3-nitro group)<br>R$^1$ = 2-{N—benzyl-N—(3-phenylpropyl)-amino}ethyl group<br>R$^2$ = isopropyl group | 62 | pale yellow oil | 1730 | 1.14(3H,d,J=6Hz), 1.25(3H,d,J=6Hz), 1.72–1.85(2H,m), 2.35(3H,s), 2.43(3H,s), 2.50–2.63(4H,m), 2.79(2H,t,J=6Hz), 3.62(2H,s), 4.08–4.25(2H,m), 4.30(2H,t,J=5Hz), 6.23(1H,s), 7.06–8.05(14H,m) | |
| 38 | (3-nitro group)<br>R$^1$ = 2-{N—benzyl-N—3-phenylpropyl)-amino}ethyl group<br>R$^2$ = ethyl group | 40 | pale yellow oil | 1730 1710 | 1.22(3H,t,J=7Hz), 1.70–1.90(2H,m), 2.35(3H,s), 2.44(3H,s), 2.50–2.65 (4H,m), 2.80(2H,t,J=5Hz), 3.62(2H,s), 4.08–4.25(2H,m), 4.30(2H,t,J=5Hz), 6.26(1H,s), 7.05–8.20(14H,m) | |
| 39 | (2-nitro group)<br>R$^1$ = 2-{N—benzyl-N—(3-phenylpropyl)-amino}ethyl group<br>R$^2$ = isopropyl group | 82 | pale yellow oil | 1730 1700 | 1.03(3H,d,J=6Hz), 1.25(3H,d,J=6Hz), 1.70–1.85(2H,m), 2.28(3H,s), 2.45(3H,s), 2.45–2.62(4H,m), 2.77(2H,t,J=6Hz), 3.61(2H,s), 4.08–4.38(2H,m), 4.91–5.08(1H,m), 6.84(1H,s), 7.04–7.80(14H,m) | |
| 40 | (2-nitro group)<br>R$^1$ = 2-{N—benzyl-N—(3-phenylpropyl)-amino}ethyl group<br>R$^2$ = ethyl group | 49 | pale yellow oil | 1730 1700 | 1.19(3H,t,J=7Hz), 1.70–1.83(2H,m), 2.30(3H,s), 2.44(3H,s), 2.47–2.60(4H,m), 2.78(2H,t,J=6Hz), 3.61(2H,s), 4.04–4.22(3H,m), 4.32(1H,m), 6.84(1H,s), 7.07–7.78(14H,m) | |
| 41 | (2-nitro group)<br>R$^1$ = 2-{4-(3,3-diphenylpropyl)-1-piperazinyl}ethyl group<br>R$^2$ = cyclopropylmethyl group | 81 | pale yellow oil | 1725 1700 | 0.10–0.25(2H,m), 0.35–0.55(2H,m), 1.00–1.20(1H,s), 2.15–2.80(14H,m), 2.34(3H,s), 2.45(3H,s), 3.75–4.52(5H,m), 6.86(1H,s), 7.10–7.57(13H,m), 7.73(1H,d,J=7Hz) | |
| 42 | (2-nitro group)<br>R$^1$ = 2-{4-(4-chloro-benzhydryl)-1-piperazinyl}ethyl group<br>R$^2$ = cyclopropylmethyl group | 30 | pale yellow oil | 1735 1710 | 0.12–0.20(2H,m), 0.37–0.48(2H,m), 1.01–1.12(1H,m), 2.23–2.40(4H,m), 2.34(3H,s), 2.42–2.52(4H,m), 2.47(3H,s), 2.57–2.74(2H,m), 3.82–3.96(2H,m), 4.08–4.19(1H,m), 4.13(1H,s), 4.36–4.45(1H,m), 6.86(1H,s), 7.14–7.76(13H,m) | |
| 43 | (2-nitro group)<br>R$^1$ = 2-{4-(9-fluorenyl)-1-piperazinyl}ethyl group<br>R$^2$ = cyclopropylmethyl group | 50 | pale yellow oil | 1740 1710 | 0.12–0.20(2H,m), 0.37–0.49(2H,m), 1.01–1.13(1H,m), 2.34(3H,s), 2.40–2.52(4H,m), 2.44(3H,s), 2.53–2.73(6H,m), 3.82–3.96(2H,m), 4.11–4.19(1H,m), 4.33–4.42(1H,m), 4.80(1H,s), 6.84(1H,s), 7.23–7.74(12H,m) | |
| 44 | (2-nitro group)<br>R$^1$ = 2-{4-(4-benzyloxy-benzyl)-1- | 54 | pale yellow oil | 1740 1710 | 0.13–0.22(2H,m), 0.38–0.51(2H,m), 1.05–1.14(1H,m), 2.25–2.42(4H,m), 2.36(3H,s), 2.43–2.55(4H,m), 2.47 | |

TABLE 2-continued (1)

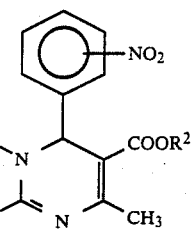

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | Elemental analysis |
|---|---|---|---|---|---|---|
| | piperazinyl}ethyl group<br>R$^2$ = cyclopropylmethyl group | | | | (3H,s), 2.57–2.74(2H,m), 3.38(2H,s), 3.84–3.98(2H,m), 4.10–4.19(1H,m), 4.38–4.47(1H,m), 5.04(2H,s), 6.87(1H,s), 6.91(2H,d,J=9Hz), 7.20(2H,d,J=1Hz), 7.23–7.77(9H,m) | |
| 45 | (2-nitro group)<br>R$^1$ = 2-{N—benzyl-N—(2-naphthylmethyl)-amino}ethyl group<br>R$^2$ = isopropyl group | 47 | pale yellow crystal m.p. 85–89° (diisopropyl-ether/n-hexane) | 1725<br>1695 | 1.04(3H,d,J=6Hz), 1.23(3H,d,J=6Hz), 2.23(3H,s), 2.50(3H,s), 2.85(2H,t,J=6Hz), 3.68(2H,s), 3.79(2H,s), 4.18–4.42(2H,m), 5.01(1H,m), 6.85(1H,s), 7.18–8.88(16H,m) | |
| 46 | (2-nitro group)<br>R$^1$ = 2-(N,N—dibenzyl-amino)ethyl group<br>R$^2$ = n-propyl group | 61 | pale yellow oil | 1730<br>1700 | 0.76(3H,t,J=7Hz), 1.50–1.70(2H,m), 2.26(3H,s), 2.48(3H,s), 2.80(2H,t,J=6Hz), 3.61(4H,brs), 4.04(2H,t,J=6Hz), 4.15–4.38(2H,m), 6.82(1H,s), 7.15–7.78(14H,m) | |
| 47 | (2-nitro group)<br>R$^1$ = 2-(N,N—dibenzyl-amino)ethyl group<br>R$^2$ = n-butyl group | 66 | pale yellow oil | 1725<br>1705 | 0.81(3H,t,J=7Hz), 1.05–1.28(2H,m), 1.48–1.62(2H,m), 2.26(3H,s), 2.48(3H,s), 2.80(2H,t,J=6Hz), 3.61(4H,brs), 4.02–4.12(2H,m), 4.13–4.38(2H,m), 6.81(1H,s), 7.15–7.75(14H,m) | |
| 48 | (2-nitro group)<br>R$^1$ = 2-(N,N—dibenzyl-amino)ethyl group<br>R$^2$ = methyl group | 41 | pale yellow crystal m.p. 103–104° C. (ether/n-hexane) | 1730<br>1710 | 2.30(3H,s), 2.46(3H,s), 2.70–2.88(2H,m), 3.60(4H,m), 3.66(3H,s), 4.15–4.40(2H,m), 6.79(1H,s), 7.10–7.75(14H,m) | |
| 49 | (2-nitro group)<br>R$^1$ = 2-(N,N—dibenzyl-amino)ethyl group<br>R$^2$ = isopropyl group | 28 | pale yellow crystal m.p. 102–103° C. (CHCl$_3$/n-hexane) | 1720<br>1700 | 1.04(3H,d,J=6Hz), 1.25(3H,d,J=6Hz), 2.44(3H,s), 2.48(3H,s), 2.80(2H,t,J=6Hz), 3.62(4H,s), 4.14–4.39(2H,m), 4.95–5.10(1H,m), 6.83(1H,s), 7.15–7.80(14H,m) | |
| 50 | (2-nitro group)<br>R$^1$ = 2-(N—benzyl-N—phenylamino)ethyl group<br>R$^2$ = isopropyl group | 22 | pale yellow crystal m.p. 121–123° C. (CHCl$_3$/n-hexane) | 1730<br>1710 | 1.04(3H,d,J=6Hz), 1.28(3H,d,J=6Hz), 2.21(3H,s), 2.44(3H,s), 3.62–3.91(2H,m), 4.25–4.53(2H,m), 4.60(2H,s), 4.95–5.10(1H,m), 6.60–6.80(4H,m), 7.04–7.82(11H,m) | |
| 51 | (2-nitro group)<br>R$^1$ = 2-{N—benzyl-N—(2-naphtylmethyl)-amino}ethyl group<br>R$^2$ = cyclopropylmethyl group | 5 | pale yellow oil | 1730<br>1700 | 0.05–0.15(2H,m), 0.35–0.45(2H,m), 1.00–1.15(1H,m), 2.25(3H,s), 2.47(3H,s), 2.72(2H,t,J=5Hz), 3.60(2H,t,J=5Hz), 3.67(2H,s), 3.78(2H,s), 4.18–4.42(2H,m), 6.85(1H,s), 7.15–7.90(16H,m) | |
| 52 | (2-nitro group)<br>R$^1$ = 2-(N,N—dibenzyl-amino)ethyl group<br>R$^2$ = cyclopropylmethyl group | 25 | pale yellow oil | 1730<br>1710 | 0.07–0.22(2H,m), 0.35–0.50(2H,m), 0.99–1.14(1H,m), 2.27(3H,s), 2.48(3H,s), 2.80(2H,t,J=6Hz), 3.61(4H,s), 3.81–3.96(2H,m), 4.12–4.40(2H,m), 6.85(1H,s), 7.11–7.79(14H,m) | |
| 53 | (2-nitro group)<br>R$^1$ = 2-{N—phenyl-N—(3-phenylpropyl)-amino}ethyl group<br>R$^2$ = isopropyl group | 41 | yellow oil | 1720<br>1690 | 1.05(3H,d,J=6Hz), 1.29(3H,d,J=6Hz), 1.82–1.99(2H,m), 2.23(3H,s), 2.45(3H,s), 2.65(2H,t,J=8Hz), 3.33(2H,t,J=8Hz), 3.46–3.75(2H,m), 4.18–4.40(2H,m), 4.95–5.10(1H,m), 6.53–6.71(3H,m), 6.78(1H,s), 7.03–7.81(11H,m) | |
| 54 | (2-nitro group)<br>R$^1$ = 2-{N—phenyl-N—(2-phenylethyl)-amino}ethyl group<br>R$^2$ = isopropyl group | 40 | yellow oil | 1730<br>1710 | 1.04(3H,d,J=6Hz), 1.27(3H,d,J=6Hz), 2.23(3H,s), 2.44(3H,s), 2.87(2H,t,J=8Hz), 3.40–3.69(4H,m), 4.14–4.36(2H,m), 4.95–5.08(1H,m), 6.60–6.82(4H,m), 7.09–7.80(11H,m) | |
| 55 | (2-nitro group)<br>R$^1$ = 2-(N,N—dibenzyl-amino)ethyl group<br>R$^2$ = isobutyl group | 10 | pale yellow oil | 1730<br>1705 | 0.72(3H,d,J=7Hz), 0.79(3H,d,J=7Hz), 1.85–1.95(1H,m), 2.25(3H,s), 2.49(3H,s), 2.80(2H,t,J=6Hz), 3.61(4H,s), 3.79–3.95(2H,m), 4.14–4.25(1H,m), 4.25–4.38(1H,m), | |

TABLE 2-continued

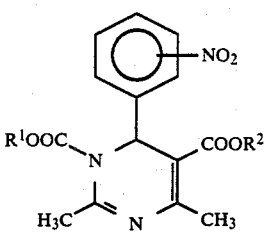
(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | Elemental analysis |
|---|---|---|---|---|---|---|
| 56 | (2-nitro group) R$^1$ = 2-(N,N—dibenzyl-amino)ethyl group R$^2$ = n-heptyl group | 45 | pale yellow oil | 1730 1705 | 6.82(1H,s), 7.15–7.75(14H,m) 0.84(3H,t,J=7Hz), 1.0–1.3(8H,m), 1.5–1.7(2H,m), 2.25(3H,s), 2.48(3H,s), 2.80(2H,t,J=6Hz), 3.61(4H,s), 4.0–4.15(2H,m), 4.15–4.25(1H,m), 4.25–4.4(1H,m), 6.81(1H,s), 7.2–7.75(14H,m) | |
| 57 | (2-nitro group) R$^1$ = 2-{N—benzyl-N—(3-phenylpropyl)-amino}ethyl group R$^2$ = methyl group | 36 | pale yellow oil | 1730 1710 | 1.65–1.85(2H,m), 2.33(3H,s), 2.43(3H,s), 2.45–2.60(4H,m), 2.78(2H,t,J=6Hz), 3.60(2H,br,s), 3.64(2H,s), 4.12–4.38(2H,m), 6.81(1H,s), 7.05–7.75(14H,m) | |
| 58 | (2-nitro group) R$^1$ = 2-{N—phenyl-N—(2-pyridylmethyl)-amino}ethyl group R$^2$ = isopropyl group | 35 | pale yellow crystal m.p. 133–136° C. (CHCl$_3$/n-hexane) | 1720 1700 | 1.04(3H,d,J=6Hz), 1.28(3H,d,J=6Hz), 2.22(3H,s), 2.44(3H,s), 3.71–3.98(2H,m), 4.30–4.56(2H,m), 4.69(2H,s), 4.95–5.08(1H,m), 6.60–6.78(4H,m), 7.02–8.59(10H,m) | |
| 59 | (2-nitro group) R$^1$ = 2-(N—benzyl-N—phenylamino)ethyl group R$^2$ = n-heptyl group | 57 | pale yellow oil | 1735 1705 | 0.85(3H,t,J=7Hz), 1.0–1.3(8H,m), 1.50–1.65(2H,m), 2.23(3H,s), 2.45(3H,s), 3.65–3.78(1H,m), 3.78–3.90(1H,m), 4.0–4.16(2H,m), 4.26–4.36(1H,m), 4.40–4.52(1H,m), 4.59(2H,s), 6.61–7.78(15H,m) | |
| 60 | (2-nitro group) R$^1$ = 2-(N—benzyl-N—phenylamino)ethyl group R$^2$ = isobutyl group | 17 | pale yellow crystal m.p. 129–131° C. (ether/n-hexane) | 1735 1710 | 0.74(3H,d,J=7Hz), 0.81(3H,d,J=7Hz), 1.85–1.97(1H,m), 2.23(3H,s), 2.46(3H,s), 3.65–3.78(1H,m), 3.78–3.96(1H,m), 4.25–4.38(1H,m), 4.38–4.51(1H,m), 4.59(2H,s), 6.60–6.78(15H,m) | |
| 61 | (2-nitro group) R$^1$ = 2-(N,N—dibenzyl-amino)ethyl group R$^2$ = ethyl group | 60 | pale yellow crystal m.p. 77–79° C. (ether/n-hexane) | 1725 1705 | 1.19(3H,t,J=7Hz), 2.27(3H,s), 2.47(3H,s), 2.80(2H,t,J=6Hz), 3.61(4H,s), 4.05–4.40(4H,m), 6.82(1H,s), 7.18–7.80(14H,m) | |
| 62 | (2-nitro group) R$^1$ = 2-{N—benzyl-N—(2-phenylethyl)-amino}ethyl group R$^2$ = isopropyl group | 31 | pale yellow oil | 1730 1710 | 1.02(3H,d,J=6Hz), 1.23(3H,d,J=6Hz), 2.26(3H,s), 2.47(3H,s), 2.74(4H,s), 2.85(2H,t,J=6Hz), 3.69(2H,s), 4.10–4.21(1H,m), 4.27–4.39(1H,m), 4.91–5.09(1H,m), 6.84(1H,s), 7.05–7.80(14H,m) | |
| 63 | (2-nitro group) R$^1$ = 2-(2-thienyl)ethyl group R$^2$ = cyclopropylmethyl group | 18 | pale yellow crystal m.p. 95–97° C. (diisopropyl ether) | 1725 1700 | 0.09–0.30(2H,m), 0.38–0.58(2H,m), 1.02–1.23(1H,m), 2.28(3H,s), 2.46(3H,s), 3.25(2H,t,J=7Hz), 3.85–4.05(2H,m), 4.30–4.55(2H,m), 6.80–7.00(3H,m), 7.10–7.22(1H,m), 7.35–7.60(3H,m), 7.72–7.85(1H,m) | |
| 64 | (2-nitro group) R$^1$ = 2-(2-benz-1,3-thiazolylthio)ethyl group R$^2$ = cyclopropylmethyl group | 76 | pale yellow oil | 1720 1695 | 0.07–0.28(2H,m), 0.37–0.60(2H,m), 1.03–1.21(1H,m), 2.38(3H,s), 2.41(3H,s), 3.55–3.72(1H,m), 3.75–4.02(3H,m), 4.40–4.56(1H,m), 4.60–4.77(1H,m), 6.84(1H,s), 7.17–7.60(5H,m), 7.65–7.95(3H,m) | |
| 65 | (2-nitro group) R$^1$ = 2-{N,N—bis(2-phenylethyl)amino}-ethyl group R$^2$ = isopropyl group | 74 | pale yellow oil | 1725 1695 | 1.02(3H,d,J=7Hz), 1.24(3H,d,J=6Hz), 2.30(3H,s), 2.46(3H,s), 2.60–2.95(10H,m), 4.04–4.19(1H,m), 4.25–4.40(1H,m), 4.90–5.10(1H,m), 6.85(1H,s), 7.05–7.82(14H,m) | |
| 66 | (2-nitro group) R$^1$ = 2-{N,N—bis(3-phenylpropyl)-amino}ethyl group R$^2$ = isopropyl group | 83 | pale yellow oil | 1730 1700 | 1.04(3H,d,J=6Hz), 1.27(3H,d,J=6Hz), 1.61–1.82(4H,m), 2.32(3H,s), 2.42(3H,s), 2.49(4H,t,J=7Hz), 2.57(4H,t,J=7Hz), 2.74(2H,t,J=7Hz), 4.05–4.20(1H,m), 4.23–4.38(1H,m), 4.92–5.10(1H,m), 6.86(1H,s), 7.05–7.80(14H,m) | |
| 67 | (2-nitro group) R$^1$ = 2-{N—benzyl-N— | 24 | pale yellow crystal | 1720 1695 | 1.04(3H,d,J=7Hz), 1.25(3H,d,J=6Hz), 2.28(3H,s), 2.48(3H,s), | |

TABLE 2-continued

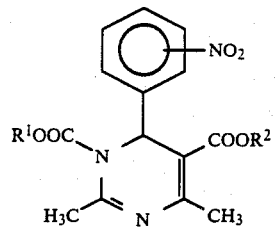
(1)

| Ex. No. | Compound (1) (position of nitro group) | Yield (%) | Description (m.p., if any) | IR spectrum (cm$^{-1}$) as measured in CHCl$_3$ | NMR spectrum (CDCl$_3$, δ ppm, 270 MHz) | Elemental analysis |
|---|---|---|---|---|---|---|
| | (2-thienylmethyl)-amino}ethyl group R$^2$ = isopropyl group | | m.p. 89–91° C. (diisopropyl ether) | | 2.84(2H,d,J=6Hz), 3.66(2H,s), 3.83(2H,s), 4.13–4.28(1H,m), 4.29–4.44(1H,m), 4.92–5.10(1H,m), 6.80–6.96(3H,m), 7.12–7.58(9H,m), 7.70–7.80(1H,m) | |
| 68 | (2-nitro group) R$^1$ = 2-{N—benzyl-N—2-pyridylmethyl)-amino}ethyl group R$^2$ = isopropyl group | 86 | pale yellow crystal m.p. 116–118° C. (diisopropyl ether) | 1725 1695 | 1.04(3H,d,J=6Hz), 1.25(3H,d,J=6Hz), 2.25(3H,s), 2.48(3H,s), 2.87(2H,t,J=6Hz), 3.68(2H,s), 3.81(2H,s), 4.16–4.29(1H,m), 4.29–4.42(1H,m), 4.92–5.11(1H,m), 6.83(1H,s), 7.08–7.82(12H,m), 8.45–8.53(1H,m) | |
| 69 | (3-nitro group) R$^1$ = 2-(N,N—dibenzyl-amino)ethyl group R$^2$ = isopropyl group | 86 | pale yellow oil | 1735 1710 | 1.15(3H,d,J=6Hz), 1.26(3H,d,J=6Hz), 2.32(3H,s), 2.46(3H,s), 2.75–2.85(2H,m), 3.62(4H,s), 4.33(2H,t,J=6Hz), 5.00–5.10(1H,m), 6.25(1H,s), 7.20–8.15(14H,m) | |
| 70 | (3-nitro group) R$^1$ = 2-(N—benzyl-N—phenylamino)ethyl group R$^2$ = isopropyl group | 66 | pale yellow oil | 1730 1710 | 1.17(3H,d,J=6Hz), 1.27(3H,d,J=6Hz), 2.35(3H,s), 2.43(3H,s), 3.70–3.85(2H,m), 4.35–4.60(2H,m), 4.58(2H,s), 5.00–5.10(1H,m), 6.20(1H,s), 6.65–8.15(14H,m) | |
| 71 | (2-nitro group) R$^1$ = 2-(N—benzyl-N—phenylamino)ethyl group R$^2$ = methyl group | 42 | pale yellow crystal m.p. 125–126° C. (CHCl$_3$/n-hexane) | 1730 1705 | 2.27(3H,s), 2.43(3H,s), 3.67(3H,s), 3.60–3.90(2H,m), 4.28–4.55(2H,m), 4.59(2H,brs), 6.71(1H,s), 6.60–7.78(14H,m) | |
| 72 | (2-nitro group) R$^1$ = 2-{N—benzyl-N—(2-naphtylmethyl)-amino}ethyl group R$^2$ = methyl group | 66 | pale yellow crystal m.p. 131–133° C. ethyl acetate-n-hexane-methanol) | 1730 1710 | 2.28(3H,s), 2.45(3H,s), 2.80–2.95(2H,m), 3.64(3H,s), 3.65(2H,s), 3.77(2H,s), 4.20–4.45(2H,m), 6.79(1H,s), 7.20–7.90(16H,m) | |
| 73 | (2-nitro group) R$^1$ = 2-{N—benzyl-N—(2-naphtylmethyl)-amino}ethyl group R$^2$ = ethyl group | 15 | pale yellow oil | 1730 1710 | 1.17(3H,t,J=7Hz), 2.25(3H,s), 2.46(3H,s), 2.85(2H,t,J=6Hz), 3.66(2H,brs), 3.77(2H,brs), 4.15–4.42(4H,m), 6.83(1H,s), 7.15–7.85(16H,m) | |
| 74 | (2-nitro group) R$^1$ = 2-{N,N bis(2-naphtylmethyl)-amino ethyl group R$^2$ = isopropyl group | 45 | pale yellow crystal m.p. 96–99° C. (diisopropyl ether) | 1720 1695 | 1.01(3H,d,J=6Hz), 1.19(3H,d,J=6Hz), 2.20(3H,s), 2.46(3H,s), 2.90(2H,t,J=6Hz), 3.82(4H,s), 4.17–4.46(2H,m), 4.90–5.08(1H,m), 6.84(1H,s), 7.28–7.90(18H,m) | |

EXAMPLE 75

The coronary vascular dilative effect of 3N-substituted 3,4-dihydropyrimidine derivatives was tested.

Test method:

Heartley guinea pigs (weight 400–500 g) were killed by a blow on the head and their hearts were immediately isolated. The hearts were perfused with Krebs-Henseleit solution bubbled with a mixture of 95% O$_2$+5% CO$_2$ and maintained at 37° C. at a constant rate of 6 ml/minute according to the Langendorff's method [J. Pharmacol. Methods 2, 143 (1979)]. The perfusion pressure was measured by a pressure transducer continuously. Samples were prepared by emulsifying 1 mg of a test compound in 1 ml of a mixture of dimethylsulfoxide and physiological saline solution (1:9) and diluting with physiological saline solution to the predetermined concentration. 0.1 ml of the diluted solution was administered into the coronary artery via a rubber tube connected to an aorta cannula to obtain ED$_{50}$ (μg/heart) data as shown in Table 3. The numbers of the compounds in the Table correspond respectively to those of the working examples described above.

TABLE 3

| Compound (Ex. No.) | 1 | 2 | 3 | 5 | 6 | 7 |
|---|---|---|---|---|---|---|
| ED$_{50}$ (μg/heart) | 0.013 | 0.52 | 0.0095 | 0.036 | 0.0092 | 0.0012 |
| Compound (Ex. No.) | 9 | 10 | 11 | 21 | 24 | 27 |
| ED$_{50}$ | 0.10 | 0.060 | 0.030 | 0.45 | 0.01 | 0.029 |

TABLE 3-continued

| Compound (Ex. No.) | 1 | 2 | 3 | 5 | 6 | 7 |
|---|---|---|---|---|---|---|
| (μg/heart) | | | | | | |

EXAMPLE 76

The pharmacological effect ($ED_{30}$) of the compounds of the present invention with respect to the vascular resistance of the vertebral artery in anesthetized dogs was treated by the following procedure.

Test method:

Adult dogs of either sex (7–14 kg in body weight) were anesthetized with at first thiopental sodium (35 mg/kg, intraperitoneal), anesthetized with urethane (400 mg/kg, intravenous) and chloralose (60 mg/kg, intravenous) and kept under artificial respiration throughout the experiment. After thoracotomy at the left first intercostal space, the vertebral artery was exposed and blood flow was measured with intracorporeal flow probe connected to an electromagnetic flowmeter (MF-27, Nihon Kohden).

At the same time, continuous measurement of the following parameters was made: systemic blood pressure (mean pressure) at the right femoral artery, the limb lead II ECG, the heart rate with a tachometer triggered by the R wave of ECG, and the vascular resistance determined by loading a electronic divider unit (EO-601 G, Nihon Kohden) with the mean values of blood pressure and vertebral artery blood flow. All of these parameters were recorded simultaneously on a polygraph (RM-600, Nihon Kohden).

All the test compounds were injected through a cannula inserted into the femoral vein.

The $ED_{30}$ (μg/kg) values obtained by intravenous injection are listed in Table 4, wherein the Compound Numbers are keyed to the Example Numbers.

TABLE 4

| Compound (Ex. No.) | 1 | 2 | 3 | 5 | 6 | 7 | 8 |
|---|---|---|---|---|---|---|---|
| $ED_{30}$ (μg/kg) | 0.58 | 0.84 | 0.75 | 2.4 | 1.4 | 0.71 | 4.1 |
| 9 | 10 | 11 | 14 | 15 | 16 | 17 | 19 |
| 3.9 | 0.54 | 0.55 | 2.1 | 2.5 | 3.8 | 3.4 | 1.4 |
| 20 | 21 | 26 | 28 | 29 | 30 | 32 | 35 |
| 4.0 | 2.0 | 4.1 | 4.2 | 2.5 | 0.60 | 3.2 | 4.2 |
| 38 | 39 | 40 | 45 | 46 | 48 | 49 | 50 |
| 4.2 | 2.3 | 1.5 | 1.8 | 2.0 | 2.0 | 2.8 | 0.74 |
| 52 | 53 | 54 | 55 | 57 | 58 | 60 | 61 |
| 1.5 | 2.5 | 1.4 | 3.8 | 0.48 | 2.5 | 1.7 | 1.4 |
| 62 | 63 | 64 | 67 | 68 | 70 | 71 | |
| 1.2 | 1.3 | 0.93 | 1.0 | 4.4 | 3.0 | 5.0 | |

EXAMPLE 77

Selected compounds of the present invention were tested for their ability to reduce the resistance of the vertebral artery in anesthetized dogs.

Test method:

The animals were injected with the $ED_{30}$ doses of test compounds and the time course of changes in the vasucular resistance were studied as shown schematically in FIG. 1. From the curve shown in FIG. 1, the values of $T_{\frac{1}{2}}$ (min) (the time to reach 50% of the resistance drop). The results are shown in Table 5, in which the compound numbers correspond to the Example numbers.

TABLE 5

| Compound No | 28 | 29 | 32 | 33 | 36 | 37 | 38 |
|---|---|---|---|---|---|---|---|
| $T_{\frac{1}{2}}$ (min.) | 13.5 | 9.5 | 7.0 | 30.5 | 12.0 | 10.3 | 8.0 |
| Compound No. | 39 | 45 | 47 | 52 | 53 | 55 | 66 |
| $T_{\frac{1}{2}}$ (min.) | 7.0 | 15.6 | 13.0 | 8.0 | 7.7 | 9.2 | 11.9 |

EXAMPLE 78

A selected compound of the present invention was tested for its hypotensive action in conscious spontaneously hypertensive rats (SHR).

Test method:

A group of 17 to 20-week old male SHR were anesthetized with ether and a cannula was inserted into the left femoral artery. At least one day after the operation, the cannula was connected to a pressure transducer and the blood pressure was measured continuously under conscious and unrestrained condition, thereby obtaining the data shown in Table 6. The test compound as clear solution dissolved in 10% ethanol was administered orally at a dose of 10 mg/kg (body weight) to each animal fasted overnight.

TABLE 6

| Compound | Blood pressure decrease (%) | |
|---|---|---|
| No. | maximum decrease | 6 hours |
| 28 | in 2 hrs. 35% | 10–20% |

EXAMPLE 79

The acute toxicity ($LD_{50}$) data of compound No. 28 of the present invention as administered to two groups of 5 or 6-week old male ddY mice were obtained by the Litchfield-Wilcoxon method. The results are shown in Table 7. One group of mice was fasted overnight prior to oral administration. To each group of mice, the test compound was administered in the form of emulsion in 10% dimethyl sulfoxide.

TABLE 7

| Compound | $LD_{50}$ (mg/kg) | |
|---|---|---|
| No. | intravenous | oral |
| 28 | 180–200 | >1,000 |

The compounds of this invention have a strong and long-lasting vasodilative effect. Therefore said compounds are considered to be useful as agents for treating disorders of the cardiovascular system such as angina pectoris, arrhythmia, hypertension or disturbance of cerebral circulation. Such disorders can be treated by administering the compound of the present invention, at a low dose level and at infrequent interval. This will make sure that treatment of such disorders can be done safely and easily.

We claim:

1. A N-substituted 3,4-dihydropyrimidine derivative of the formula (1):

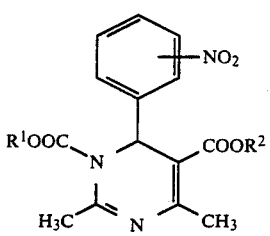

wherein R¹ is —(CH$_2$)$_n$—X; X is

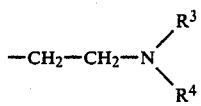

wherein
- R$_3$ is C$_{1-4}$ alkyl which may be mono or di-substituted with phenyl or naphthyl, phenyl, C$_{9-12}$ arylalkenyl, thienylmethyl or pyridylmethyl;
- R$_4$ is C$_{1-4}$ alkyl which may be mono or di-substituted with phenyl or naphthyl, phenyl or C$_{9-12}$ arylalkenyl,
- with the proviso that when one of R$^3$ and R$^4$ is said alkyl and the other is aralkyl, said aralkyl may be substituted with methoxy, chloro, nitro or fluoro, or
- X is benzylpyrrolidinylmethyl, benzthiazolylthioethyl, morpholinoethyl, 2-tetrahydroisoquinolinylethyl, pyridylethyl, thienylethyl, 4-substituted-1-piperazinylethyl wherein the substituent is C$_{1-4}$ alkyl which may be substituted with phenyl, benzyloxyphenyl, or diphenyl, trifluoromethylphenyl, fluorenyl or trimethoxycinnamoyl;
- n is an integer from 0 to 3;
- R$^2$ is C$_1$–C$_{13}$ straight alkyl, C$_3$–C$_{13}$ branched or cyclic alkyl, or C$_4$–C$_{13}$ cyclo-straight alkyl, or C$_7$–C$_{13}$ aralkyl, or a pharmacologically acceptable acid addition salt thereof.

2. A vasodilating composition comprising an effective amount of a N-substituted 3,4-dihydropyrimidine derivative of the formula (1):

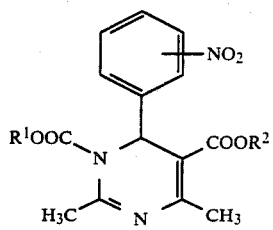

wherein R¹ is —(CH$_2$)$_n$—X; X is

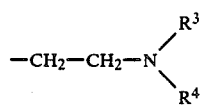

wherein
- R$_3$ is C$_{1-4}$ alkyl which may be mono or di-substituted with phenyl or naphthyl, phenyl, C$_{9-12}$ arylalkenyl, thienylmethyl or pyridylmethyl;
- R$_4$ is C$_{1-4}$ alkyl which may be mono or di-substituted with phenyl or naphthyl, phenyl or C$_{9-12}$ arylalkenyl,
- with the proviso that when one of R$^3$ and R$^4$ is said alkyl and the other is aralkyl said aralkyl may be substituted with methoxy, chloro, nitro or fluoro or
- X is benzylpyrrolidinylmethyl, benzthiazolylthioethyl, morpholinoethyl, 2-tetrahydroisoquinolenylethyl, pyridylethyl, thienylethyl, 4-substituted-1-piperazinylethyl wherein the substituent is C$_{1-4}$ alkyl which may be substituted with phenyl, benzyloxyphenyl or diphenyl, trifluoromethylphenyl, fluorenyl or trimethoxycinnamoyl;
- n is an integer from 0 to 3;
- R$^2$ is C$_1$–C$_{13}$ straight alkyl, C$_3$–C$_{13}$ aralkyl, or a pharmacologically acceptable acid addition salt thereof and a pharmaceutically acceptable carrier.

* * * * *